United States Patent
Fernfors

(10) Patent No.: US 7,458,959 B2
(45) Date of Patent: Dec. 2, 2008

(54) BREATHABLE ABSORBENT ARTICLE

(75) Inventor: Ingemar Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 418 days.

(21) Appl. No.: 10/323,691

(22) Filed: Dec. 20, 2002

(65) Prior Publication Data

US 2003/0125691 A1 Jul. 3, 2003

Related U.S. Application Data

(60) Provisional application No. 60/341,268, filed on Dec. 20, 2001.

(51) Int. Cl.
*A61F 13/15* (2006.01)

(52) U.S. Cl. ............ 604/385.01; 604/385.12; 604/369; 604/358; 604/367; 604/384; 604/378

(58) Field of Classification Search ............ 604/385.01, 604/385.12, 369, 358, 367, 384, 378
See application file for complete search history.

(56) References Cited

U.S. PATENT DOCUMENTS

| | | | |
|---|---|---|---|
| 4,515,595 A | | 5/1985 | Kievit et al. |
| 4,822,350 A | | 4/1989 | Ito et al. |
| 5,004,465 A | | 4/1991 | Ternstrom et al. |
| 5,196,242 A | * | 3/1993 | Vicino ............ 428/12 |
| 5,520,674 A | * | 5/1996 | Lavon et al. ............ 604/385.16 |
| 5,582,604 A | * | 12/1996 | Ahr et al. ............ 604/385.12 |
| 5,643,239 A | * | 7/1997 | Bodford et al. ............ 604/370 |
| 5,769,834 A | * | 6/1998 | Reiter et al. ............ 604/385.12 |
| 5,879,341 A | * | 3/1999 | Odorzynski et al. ......... 604/367 |
| 6,090,994 A | | 7/2000 | Chen |
| 6,128,784 A | * | 10/2000 | Frank ............ 2/102 |
| 6,221,460 B1 | * | 4/2001 | Weber et al. ............ 428/131 |
| 6,238,379 B1 | * | 5/2001 | Keuhn et al. ............ 604/367 |
| 6,450,997 B1 | * | 9/2002 | Seitz et al. ............ 604/385.01 |
| 6,483,007 B1 | | 11/2002 | Hansson et al. |

FOREIGN PATENT DOCUMENTS

| | | | |
|---|---|---|---|
| CA | 2276303 A1 | * | 2/2000 |
| WO | 96/14034 | | 5/1996 |
| WO | 2000/59436 | | 10/2000 |

\* cited by examiner

*Primary Examiner*—T. Zalukaeva
*Assistant Examiner*—Ginger T Chapman
(74) *Attorney, Agent, or Firm*—Buchanan Ingersoll & Rooney PC

(57) ABSTRACT

An absorbent article having an upper, liquid-permeable cover layer (2), a lower, liquid-impermeable backsheet (4), an absorbent body (6) arranged between the cover layer (2) and the backsheet (4), and an air-exchange system arranged between the cover layer (2) and the backsheet (4) having at least one air-exchange (5; 43) and at least one air-exchange duct (10) having a longitudinal extension and a cross-sectional area, the air-exchange duct (10) constituting a communicating duct with regard to air communication between the air-exchange (5; 43) and the surroundings of the absorbent article. The air-exchange (5; 43) comprises a material which is compressible and resilient in all directions, essentially non-absorbent and air-permeable, and the air-exchange duct (10) has a compressible and resilient, essentially non-absorbent material, the air-exchange duct displaying air-permeability.

20 Claims, 10 Drawing Sheets

BREATHABLE ABSORBENT ARTICLE

This application claims priority under 35 U.S.C. §119 to U.S. Provisional Application No. 60/341,268 entitled BREATHABLE ABSORBENT ARTICLE and filed on Dec. 20, 2001, the entire content of which is hereby incorporated by reference.

TECHNICAL FIELD

The present invention relates to an absorbent article comprising an upper, liquid-permeable cover layer, a lower, liquid-impermeable backsheet, an absorbent body arranged between the cover layer and the backsheet, and an air-exchange system arranged between the cover layer and the backsheet comprising at least one air-exchange and at least one air-exchange duct having a longitudinal extension and a cross-sectional area, the air-exchange duct constituting a communicating duct with regard to air communication between the air-exchange and the surroundings of the absorbent article.

BACKGROUND ART

The most important function of absorbent articles such as, for example, diapers, incontinence devices or sanitary towels, is to provide absorption capacity and to afford good leakage protection when bodily fluids such as urine, menstrual fluid etc. are discharged.

Another important characteristic of the absorbent article is that it is pleasant and comfortable to use.

Examples of improvements which have been made with regard to wearer comfort are: increased dryness against the body of the wearer in spite of containing large quantities of liquid, thinner and more flexible articles, and a softer surface against the body of the wearer. Articles which are designed so that unpleasant odour is reduced during use are further examples of improvements made with regard to wearer comfort. Other improvements could be enumerated.

Absorbent articles have also been improved by having been made breathable, that is the absorbent articles have been designed so that they do not function like warm and wet compresses as soon as they have become wet after the first urination or discharge of bodily fluid into the articles. A warm and wet compress is formed if a moist and impermeable absorbent article lies in contact with the skin of the wearer without the possibility of ventilation, that is without the possibility of transporting moisture away from the skin of the wearer. Articles which create warm and wet compresses during use frequently cause the wearer skin irritation problems, especially in the case of long-term use. Those articles which make it possible for moisture to be transported away are referred to within the technical field as breathable absorbent articles. Breathable absorbent articles represent a considerable improvement of the articles with regard to wearer comfort and have also brought about a marked improvement in the skin condition of the wearer during use of the absorbent articles.

The most common method of making absorbent articles breathable is to replace the liquid-impermeable and vapour-impermeable backsheet, which is normally arranged on that side of the article which faces away from the wearer during use, with a microporous liquid-impermeable backsheet which displays vapour-permeability. An example of an absorbent article with a vapour-permeable backsheet is described in, for example, the patent U.S. Pat. No. 4,822,350.

In other absorbent articles, the liquid-impermeable and vapour-impermeable backsheet has been replaced with a backsheet which has conical penetrating capillaries. In these articles, the conical capillaries are oriented so that liquid cannot pass through the capillaries, that is the smallest radius of the conical capillary is oriented towards the wet absorbent absorption core and the largest radius of the capillary is located on that surface of the backsheet which is oriented away from the wet absorbent absorption core. An example of an absorbent article which has a backsheet with conical capillaries is described in patent application WO 00/59436.

Creating an absorbent article with a backsheet which simultaneously has sufficient liquid-impermeability and sufficient breathability is the main problem in the design of the articles described above. In most cases, articles with a microporous backsheet, or with conical penetrating capillaries, have had too poor breathability because the liquid-impermeability of the backsheet was given priority over the breathability. In those cases where the breathability was given priority, major problems have arisen with liquid penetration through the breathable backsheet.

In the patent U.S. Pat. No. 6,090,994, the breathability of the absorbent article has been brought about in a completely different way. The article according to said patent has been provided with an air-exchange, wherein compressible and resilient air pockets are arranged in communication with the air which is present inside the absorption body of the absorbent article. When an article according to said patent is subjected to a pressure, for example when a wearer sits on the article, the air pockets are compressed, the volume of the air pockets being reduced. On compression, the air inside the pockets is forced out into an air-exchange duct system which communicates with the air pockets and opens adjacent to the transverse ends of the article. Arranged at the ends of the article are permeable foam/sponge materials, the air coming out of the air-exchange duct system being able to leave the article through the permeable foam/sponge materials. When the external loading is removed from the absorbent article, the air pockets recover resiliently and new air is sucked into the article via the permeable foam/sponge materials and into the air pockets via the communicating air-exchange duct system.

The compressible and resilient air pockets and the air-exchange duct system have been produced by virtue of a three-dimensional resilient framework being arranged between the absorbent body of the absorbent article and the liquid-impermeable backsheet which is oriented away from the wearer during use. One problem with breathable articles according to U.S. Pat. No. 6,090,994 is that the three-dimensional resilient framework is expensive to produce and difficult to handle in a conventional machine for manufacturing absorbent articles. The design of the three-dimensional resilient framework also means that there is a risk of the absorbent article feeling uncomfortable because the edges of the framework are relatively sharp and can press hard against the thighs of a wearer during use. Another disadvantage is that air exchange inside an absorbent article according to the invention takes place only when the article is subjected to loading essentially at right angles to its plane.

A need still exists therefore for an improved breathable absorbent article which feels comfortable for the wearer and which exchanges air both when the article is subjected to forces in its plane, such as pressure forces from the thighs of the wearer, and when the article is subjected to forces at right angles to its plane, such as forces when the wearer sits on the absorbent article.

There is also a need for a breathable absorbent article which is simple and inexpensive to manufacture and can be manufactured using materials which are conventional for absorbent articles on machines which are conventional for the manufacture of absorbent articles.

SUMMARY

By means of the present invention, however, an article of the type referred to in the introduction has been produced, which article essentially eliminates the problems associated with previously known such articles.

In this connection, an absorbent article made according to the invention is characterized mainly in that the air-exchange (5; 43) is compressible and resilient in all directions, essentially non-absorbent and air-permeable, and in that the air-exchange duct (10) comprises a compressible and resilient, essentially non-absorbent material, and in that the air-exchange duct displays air-permeability.

According to an embodiment, the air-exchange of the absorbent article has a volume which is at least two times greater than the volume of the air-exchange duct, preferably at least five times greater than the volume of the air-exchange duct, and most preferably at least seven times greater.

The air-exchange of the absorbent article can comprise an essentially non-absorbent hydrophobic fibre wadding.

The main constituent of the air-exchange is advantageously a capillary material, for example a fibre wadding, or an open-cell foamed material. The absorption body of the absorbent article also suitably consists mainly of a capillary material. In this connection, according to an embodiment, the air-exchange of the absorbent article has capillaries which are larger than the capillaries of the absorbent body.

According to an embodiment, the air-exchange of the absorbent article comprises an essentially non-absorbent foamed plastic comprising open cells.

According to an embodiment, the entire contact surface between the air-exchange and the absorbent body is open with regard to air communication. This means that air exchange between the air-exchange and the absorbent body can take place essentially freely over the entire interface between the two components.

According to an embodiment, the air-permeable non-absorbent material of the air-exchange duct comprises a strand of an essentially non-absorbent hydrophobic fibre wadding.

According to an embodiment, the air-permeable non-absorbent material of the air-exchange duct comprises a strand of essentially non-absorbent hydrophobic foamed plastic having open cells. In this connection, a foamed material with open cells is a material which allows the passage of, for example, air between the cells.

Alternatively, the non-absorbent material of the air-exchange duct can consist of a flexible tube.

The absorbent article can be provided with two air-exchange ducts which extend from the air-exchange to different places at the periphery of the absorbent article.

In this connection, one of the air-exchange ducts can be provided with an inflow valve.

It is also possible to provide one air-exchange duct of the absorbent article with an inflow valve and the other air-exchange duct with an outflow valve.

The absorbent article can also comprise at least one absorbent material piece arranged between the air-exchange duct and the liquid-impermeable backsheet.

The air-exchange duct does not have to be straight, but air-exchange ducts having a curved extension are conceivable within the scope of the invention. It is also possible to use air-exchange ducts having both straight and curved segments.

According to an embodiment of the invention, the air-exchange of the absorbent article has a curve having an S-shape.

When the absorbent article consists of a baby diaper, the air-exchange suitably has a length within the range 5-25 cm, a width within the range 3-12 cm and a thickness within the range 0.3-3 cm.

When the absorbent article consists of an incontinence device, the air-exchange suitably has a length within the range 10-50 cm, a width within the range 3-15 cm and a thickness within the range 0.3-3 cm.

The absorbent article can also consist of a sanitary towel or an incontinence device for light incontinence, the air-exchange suitably having a length within the range 2-20 cm, a width within the range 2-8 cm and a thickness within the range 0.2-3 cm.

BRIEF DESCRIPTION OF FIGURES

The invention will be described in greater detail below with reference to the illustrative embodiments which are shown in the accompanying figures, in which.

DESCRIPTION OF EMBODIMENTS

The invention relates to an absorbent article such as a diaper, an incontinence device, a sanitary towel or the like.

Figure 1:
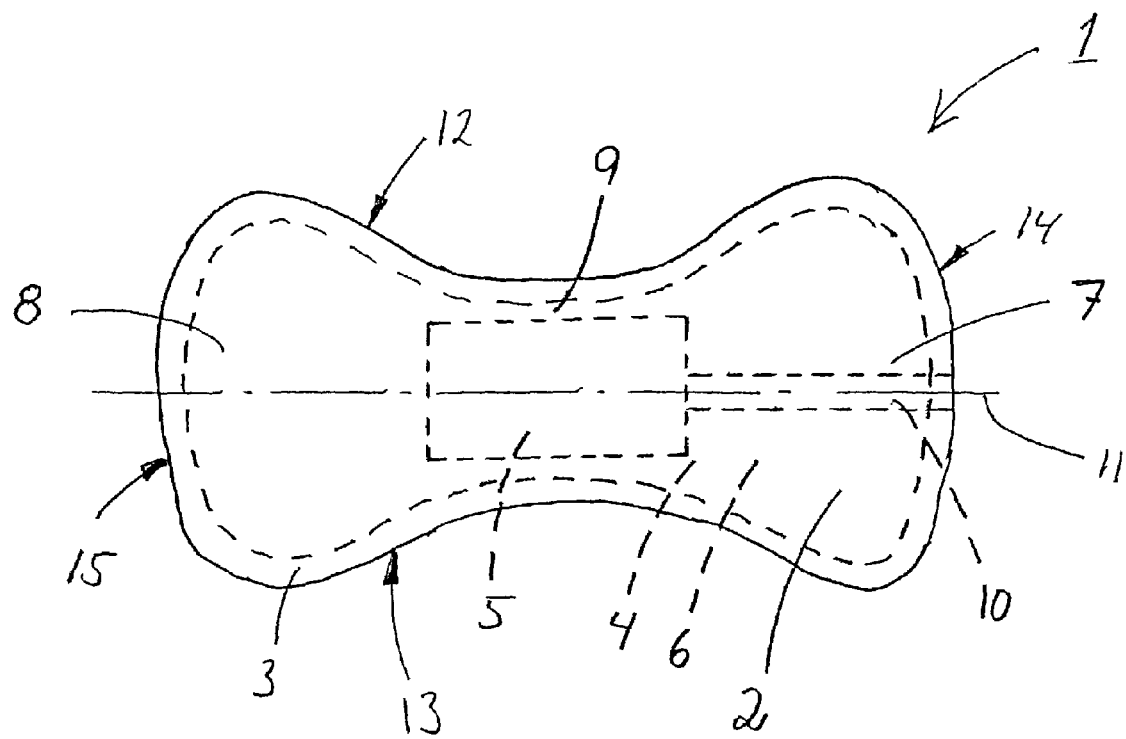
FIG. 1 shows an incontinence device for light incontinence according to a first embodiment of the invention, seen from the side which is intended to face the wearer during use.
Figure 2:
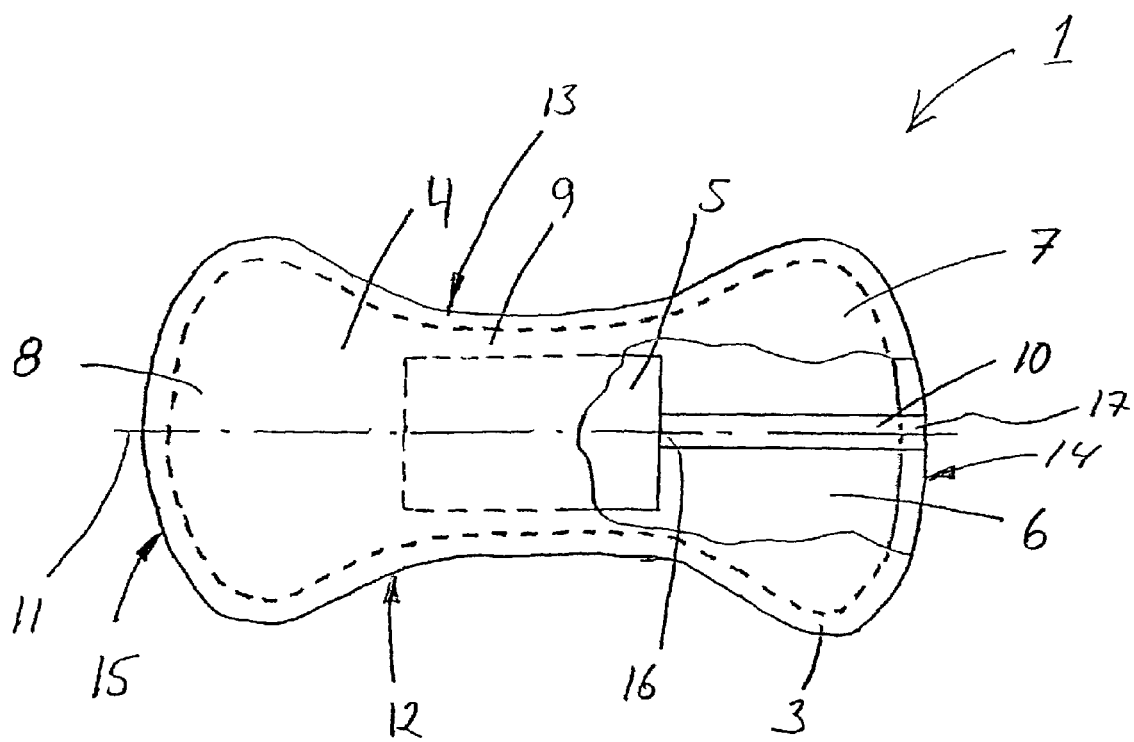
FIG. 2 shows an incontinence device for light incontinence according to a first embodiment of the invention, seen from the side which is intended to face away from the wearer during use.

The first embodiment shown in FIGS. 1 and 2 concerns an incontinence device 1 for lighter forms of incontinence.

The incontinence device 1 is hourglass-shaped and in this connection has two wider end portions 7 and 8, and a narrower crotch portion 9 located between the end portions 7 and 8. During use, the crotch portion 9 is intended to be located in the narrowest area between the thighs of the wearer and is the area of the incontinence device 1 which during normal use is wetted first by discharged bodily fluid. The incontinence device 1 has longitudinal edges 12, 13 and transverse edges 14, 15.

The incontinence device 1 comprises a liquid-permeable cover layer 2 arranged over that surface of the incontinence device 1 which is intended to face the wearer during use, a liquid-impermeable backsheet 4 arranged over that surface of the article which is intended to face away from the wearer during use, an absorption body 6 enclosed between the liquid-permeable cover layer 2 and the backsheet 4, side flaps 3 arranged outside the absorption body 6, an air-exchange 5 arranged between the liquid-impermeable backsheet 4 and the absorption body 6, and an air-exchange duct 10 arranged between the liquid-impermeable backsheet 4 and the absorption body 6.

In order to show the air-exchange 5 and the air-exchange duct 10 more clearly, a part of the liquid-impermeable backsheet 4 has not been illustrated in FIG. 2.

The liquid-permeable cover layer 2 extends outside the absorption body 6 along the entire circumference of the absorption body 6. The liquid-permeable cover layer 2 can consist of any material suitable for the purpose. Examples of commonly used liquid-permeable cover materials are non-woven textile materials, perforated plastic films, net made of plastic or textile, and liquid-permeable foam layers. Liquid-permeable cover materials which consist of continuous thin fibres extending mainly in the longitudinal or transverse direction of the article are also found. Laminates consisting of two or more of the abovementioned possible cover materials are also common, as are covers consisting of different materials within different parts of the surface.

The liquid-impermeable backsheet 4 extends outside the absorption body 6 along the entire circumference of the absorption body 6.

The liquid-impermeable backsheet 4 can also consist of a number of different materials. It is most usual for the liquid-impermeable backsheet 4 to consist of a thin liquid-impermeable plastic film, but it is also possible to use other types of liquid-impermeable materials, such as non-woven materials made liquid-impermeable by, for example, plastic coating, liquid-impermeable foam layers, liquid-impermeable glue or the like. The liquid-impermeable backsheet 4 can consist of a vapour-permeable material.

Incontinence devices of the type described by the present invention usually also comprise a fastening system for fixing the article to the underwear of the wearer. Such a fastening system usually comprises one or more glue strands arranged on the liquid-impermeable backsheet of the absorbent article and a removable protective layer arranged over the glue strands. Other types of fastening system are also conceivable. Examples of alternative fastening systems are layers of high-friction material, layers of hook-and-loop material or the like.

Incontinence devices can also exhibit side flaps for fastening the incontinence device in the briefs. Such side flaps are then arranged on each side of the absorption body, the side flaps projecting in the transverse direction from each longitudinal side edge. The side flaps have a shape and size which make it possible for them, during use, to be folded around the leg openings of the briefs and fixed to the outside of the briefs in the crotch area. The side flaps usually consist of the liquid-permeable backsheet and the liquid-permeable surface layer which are in this connection extended in the transverse direction, but can alternatively consist of separate material pieces which are attached along the side edges of the incontinence device. Such projecting side flaps are usually provided with adhesive fastening means on the surface facing away from the wearer so as to ensure that the side flaps lie against/are fixed to the outside of the briefs during use. In this connection, the fastening means is protected by removable protective layers which are intended to protect the adhesive fastening means from dirt and dust and prevent the adhesive from adhering to inappropriate surfaces or to itself until the incontinence device is to be used. As an alternative to the adhesive fastening means, fastening means which adhere mechanically can be used, for example hook-and-loop material. No fastening systems or projecting side flaps are illustrated in the figures.

The liquid-permeable cover layer 2 and the liquid-impermeable backsheet 4 are interconnected outside the absorption body 6 along essentially the entire circumference of the absorption body 6. However, the liquid-permeable cover layer 2 and the liquid-impermeable backsheet 4 are not interconnected within a small area 17 outside the absorption body 6, within which area 17 the air-exchange duct 10 opens.

The liquid-permeable cover layer 2 and the liquid-impermeable backsheet 4 can be interconnected in a number of different ways. Examples of methods of connection are gluing, hot-melting, ultrasonic welding, needling or the like.

The absorption body 6 can be constructed from one or more layers of cellulose fluff pulp. In this connection, the cellulose fluff pulp can be mixed with fibres or particles of a highly absorbent polymer material of the type which, on absorption, chemically binds large quantities of liquid, forming a liquid-containing gel. The absorption body 6 can also include additional components for improving the characteristics of the absorption body 6. Examples of such components are binding fibres, liquid-spreading layers or fibres of various types, shape-stabilizing components, reinforcing fibres or the like. The absorption body 6 can of course also consist of other types of absorption materials, such as absorbent non-woven materials, absorbent foam, textile materials, peat or mixtures of different types of absorption materials. Special layers for rapidly receiving larger quantities of liquid and temporarily storing this liquid, subsequently to transfer the temporarily stored liquid to other parts of the absorption body 6, can also be included in incontinence devices of the type specified. These receiving layers are then normally arranged between the liquid-permeable cover layer 2 and the absorption body 6 of the incontinence device 1. No receiving layer is illustrated in any of the figures.

Incontinence devices according to the invention can comprise elastics arranged outside the absorption body in those parts of the side flaps 3 of the incontinence device which run essentially in the longitudinal direction of the incontinence device. The elastics then serve as leg elastic and have the role of preventing urine leaking out at the side edges 12, 13 running in the longitudinal direction and in this way form, together with the side flaps 3, outer liquid barriers. The elastics suitably consist of one or more elastic threads which are applied in a stretched state between the liquid-permeable cover layer 2 and the liquid-impermeable backsheet 4, at least in the crotch portion 9 of the incontinence device. The elastics are suitably connected to the backsheet 4 and the liquid-permeable cover layer 2 by gluing, ultrasonic welding or the like.

In order further to prevent liquid leaking out over the edges 12-15 of the incontinence device, it is usual for incontinence devices also to be provided with inner side leakage barriers. The inner side leakage barriers are then arranged on that side of the incontinence device which is intended to face the wearer during use. The inner side leakage barriers are arranged close to the longitudinal edges 12, 13 of the absorption body and extend essentially in the longitudinal direction of the incontinence device. Each inner side leakage barrier usually consists of a double-folded material strip, the folded edge of the strip constituting the ridge of the side leakage barrier and the two longitudinal edges of the strip constituting the base of the side leakage barrier. The edges of the double-folded material strip, that is the base of the material strip, are fastened to the liquid-permeable cover layer 2 and then constitute the fastened edge of the inner side leakage barrier, the ridge of the material strip constituting the free edge of the inner side leakage barrier.

In the end portions 7, 8 of the incontinence device, the inner side leakage barriers are suitably folded down and connected to the liquid-permeable cover layer 2. The inner side leakage barriers often comprise elastic elements which are connected to the inner side leakage barriers in a prestressed state. The elastic elements are preferably arranged close to the free edges of the inner side leakage barriers. When the prestressed elastic elements are released, they contract together with the free edges of the inner side leakage barriers, the inner side leakage barriers being brought into a raised configuration away from the liquid-permeable cover layer 2, at least in the crotch portion 9 of the incontinence device. No outer liquid barriers or inner side leakage barriers or elastic elements are illustrated in any of the figures.

The incontinence device 1 is characterized mainly in that it comprises an air-exchange 5 and an air-exchange duct 10, the air-exchange duct 10 creating an air-communicating duct between the air-exchange 5 and the surrounding atmosphere of the incontinence device 1. The air-exchange 5 and the air-exchange duct 10 are arranged between the absorption body 6 and the liquid-impermeable backsheet 4.

In alternative illustrative embodiments, the air-exchange 5 and the air-exchange duct 10 can be arranged between the various layers of the absorption body 6. In certain embodiments, the air-exchange 5 and the air-exchange duct 10 can even be arranged inside the absorption body 6.

The air-exchange 5 is arranged essentially symmetrically around the longitudinal symmetry line 11 of the incontinence device 1, and essentially in the crotch portion 9 of the incontinence device 1.

The air-exchange 5 consists of an essentially non-absorbent material which is compressible and resilient in all directions. In this connection, the air-exchange 5 suitably consists of an open synthetic wadding made of, for example, polyester fibres. The wadding is of the same type as is often used in diapers and incontinence devices as liquid-isolating distance layers and liquid admission layers, and is in this connection arranged between the liquid-permeable cover layer and the absorption body.

It is essential that the air-exchange 5 according to the invention has an extremely limited ability for absorbing liquid which is bound in the absorption body 6, for which reason the design of the air-exchange with regard to material selection and degree of compression is important.

The fibres in the open synthetic wadding of the air-exchange 5 are of a hydrophobic nature and are in this connection not absorbent, for which reason liquid which is bound in the hydrophilic absorption body 6 does not tend to be transferred to the open synthetic wadding. The open synthetic wadding is moreover selected so that its capillaries are considerably larger than the capillaries in the absorption body 6, which means that capillary transport of liquid from the hydrophilic fine-capillary absorption body 6 into the coarse-capillary wadding structure of the air-exchange 5 is negligible.

Another essential characteristic of an incontinence device 1 according to the invention is that there is good air communication between the absorption body 6 and the air-exchange 5. This is ensured by the invention by virtue of the open synthetic wadding in the air-exchange 5 having extremely good air communication with the absorption body 6. In the illustrative embodiment, good air communication between the absorption body 6 and the air-exchange 5 is provided for by virtue of the air-exchange being in direct contact with the absorption body 6 over a contact surface, the entire contact surface between the air-exchange 5 and the absorption body 6 being open with regard to air communication.

When an incontinence device according to the invention has become oversaturated with urine, it can happen that the absorption body 6 is not capable of binding all the liquid in a satisfactory manner, in which case some drops of urine may be pressed out of the absorption body and end up in the air-exchange duct 10 which then becomes slightly moist. It is then important that the air-exchange 5 does not collapse. Open synthetic wadding materials of the type concerned here have the characteristic of essentially retaining their resilience and openness, at least in a slightly moist state.

Waddings made of synthetic fibres other than polyester fibres are of course also possible as a component of the air-exchange 5. Examples of other suitable fibre qualities are polypropylene fibres and polyethylene fibres. Mixtures of different synthetic fibre sorts are also possible.

It is also possible to select materials other than open hydrophobic synthetic wadding materials as the main component of the air-exchange 5. An example of a suitable material is resilient foamed plastic with open cells which are in air communication with one another and with the surroundings.

Hydrophobed resilient cellulose fibres or other types of natural fibres can also be included as materials in the air-exchange 5.

The incontinence device 1 comprises an air-exchange duct 10. In FIGS. 1 and 2, the air-exchange duct 10 extends along the symmetry line 11 of the incontinence device 1 from the air-exchange 5 to the transverse edge 14 of the article 1. In the illustrative embodiment, the air-exchange duct 10 consists of an elongate open synthetic hydrophobic wadding strand with a first end 16 which lies against the air-exchange 5, in direct contact therewith, and with an outlet 17 located at the transverse edge 14 of the incontinence device 1.

The open structure of the air-exchange duct 10 means that air passes through the material of the air-exchange duct 10 considerably easier than through other components of the incontinence device 1 such as, for example, the cellulose fluff pulp of the absorption body 6.

The air-exchange duct 10 suitably comprises, in exactly the same way as the air-exchange 5, an open synthetic wadding made of, for example, polyester fibres. It is likewise important that the air-exchange duct 10 according to the invention has an extremely limited capacity for absorbing liquid which is bound in the absorption body 6, for which reason the design of the air-exchange with regard to material selection and degree of compression is also important.

As the air-exchange duct 10 consists of an open synthetic wadding, it is of a hydrophobic nature and in this connection not absorbent, for which reason liquid which is bound in the hydrophilic absorption body 6 does not easily tend to be transferred to the open synthetic wadding.

As with the air-exchange, the capillaries of the open synthetic wadding are moreover considerably larger than the capillaries in the absorption body 6, which means that capillary transport of liquid from the hydrophilic fine-capillary absorption body 6 into the coarse-capillary wadding structure of the air-exchange duct 10 is negligible.

It is also important that the air-exchange duct 10 does not collapse if, in spite of its non-absorbent nature, it becomes slightly moist, which can happen if the absorption body 6 becomes oversaturated with urine. Open synthetic wadding materials of the type which is suitable for the air-exchange duct 10 have the characteristic of essentially retaining their resilience and openness, at least in a slightly moist state.

It is of course possible to use materials other than polyester fibres as the main component of the air-exchange duct 10. Examples of other fibre qualities are polypropylene fibres and polyethylene fibres. Mixtures of different synthetic fibre sorts are also possible.

It is also possible to select materials other than open hydrophobic synthetic wadding materials as the main component of the air-exchange duct 10. An example of a suitable material is foamed plastic with cells which are open and in air communication with one another and with the surroundings.

Hydrophobed resilient cellulose fibres can also be included as a material in the air-exchange 5.

It is also conceivable to arrange a flexible tube or the like as the air-exchange duct 10.

During use of an incontinence device 1 according to the invention, the air-exchange 5 will, owing to the movement pattern of the wearer, continuously be compressed and expanded, air exchange taking place through the air-exchange duct 10, through which air passes considerably more easily than through other parts of the absorbent article 1. When the air-exchange 5 is compressed, an air quantity corresponding to the compressed volume leaves the incontinence device 1, essentially through the air-exchange duct 10. When the compression of the incontinence device 1 ceases, the air-exchange 5, on account of its resilient structure, recovers its original volume, new air being sucked into the air-exchange 5 through the air-exchange duct 10.

In designing the air-exchange 5 and air-exchange duct 10 of the incontinence device 1, it is important that the volume of the air-exchange 5 considerably exceeds the volume of the air-exchange duct 10. A considerably greater volume of the air-exchange 5 than of the air-exchange duct 10 affords a guarantee that the majority of the air quantity which is pressed out of the air-exchange 5 actually flows through the air-exchange duct 5 and out of the incontinence device 1 and that the majority of the new air which flows back into the air-exchange 5 comes from the surroundings of the incontinence device 1.

If the volume ratio is selected disadvantageously, that is the volume of the air-exchange duct 10 is selected to be too large in relation to the volume of the air-exchange 5, the air which flows out from the air-exchange 5 will remain in the air-exchange duct 10 and flow back into the air-exchange 5 when the air-exchange 5 recovers its volume. The same moist air will then be moved to and fro between the air-exchange 5 and the air-exchange duct 10 throughout the whole time the incontinence device 1 is in use.

For baby diapers, the air-exchange/air-exchange duct volume ratio should be over 2, preferably over 5 and more preferably over 7. For large incontinence devices for heavy incontinence, the air-exchange/air-exchange duct volume ratio should be over 2, preferably over 5 and more preferably over 7. For sanitary protection means and incontinence devices 1 for light incontinence, the air-exchange 5/air-exchange duct 10 volume ratio should be over 2, preferably over 5 and more preferably over 7.

Figure 3:
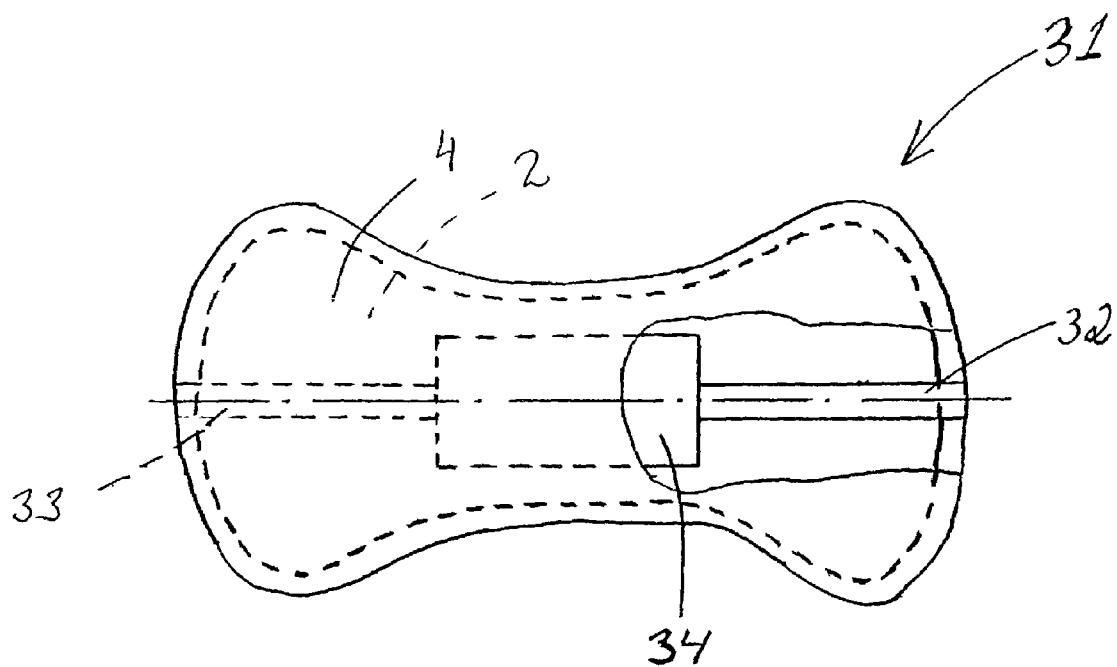
FIG. 3 shows an incontinence device for light incontinence according to a second embodiment of the invention, seen from the side which is intended to face away from the wearer during use.

FIG. 3 shows an incontinence device 31 according to a second embodiment of the invention, seen from the side which is intended to face away from the wearer during use. In order to show components which are important for the invention more clearly, a part of the liquid-impermeable backsheet 4 has not been illustrated in the figure. The incontinence device 31 comprises two air-exchange ducts 32, 33 which ensure that air can pass to and from the air-exchange 34. Both the air-exchange ducts 32, 33 are designed in the same way and comprise the same material as the air-exchange duct 10 according to the first embodiment. The advantage of providing an absorbent article with two air-exchange ducts 32, 33 is that an effective air exchange is guaranteed even if one of the two air-exchange ducts is obstructed for some reason.

Figure 4:
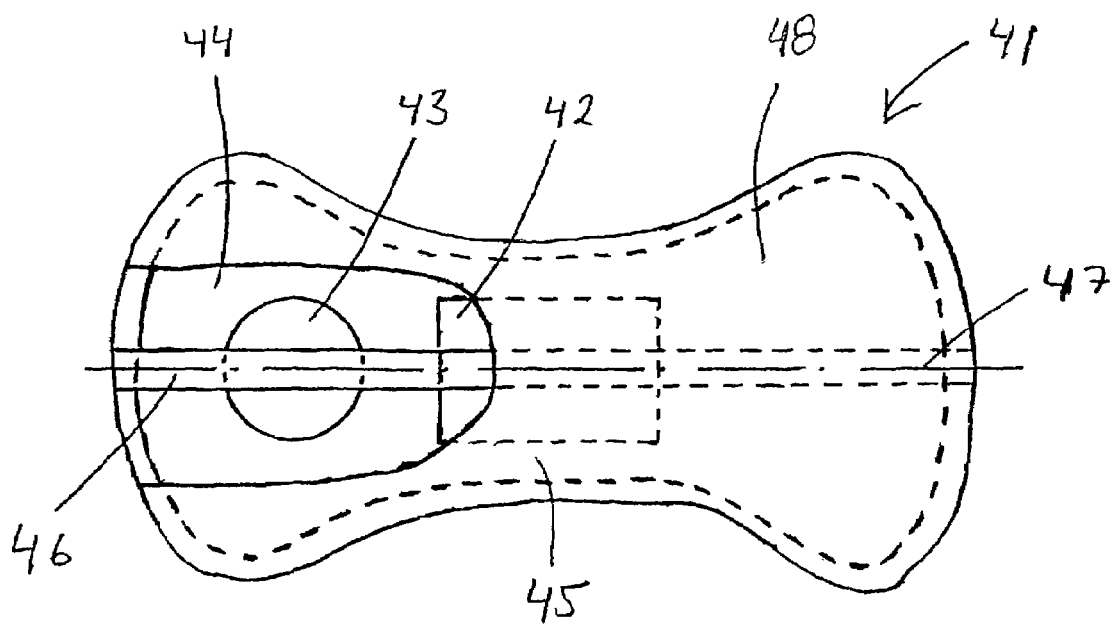
FIG. 4 shows an incontinence device for light incontinence according to a third embodiment of the invention, seen from the side which is intended to face away from the wearer during use.

FIG. 4 shows an incontinence device 41 according to a third embodiment, from the side which is intended to face away from the wearer during use. In order to show components which are important for the invention more clearly, a part of the liquid-impermeable backsheet 48 has not been illustrated in the figure.

The incontinence device 41 comprises two air-exchanges 42, 43, one 43 of the air-exchanges being arranged in one end portion 44 of the incontinence device 41 and the other 42 being arranged in the crotch portion 45 of the incontinence device 41.

The incontinence device 41 comprises one air-exchange duct 46, the air-exchange duct 46 extending along the longitudinal symmetry line 47 of the incontinence device 41 along the entire length of the incontinence device 41. The air-exchange duct 46 is arranged between the liquid-impermeable backsheet 48 and the two air-exchanges 42, 43.

Alternatively, separate air-exchange ducts which connect the respective air-exchanges 42, 43 to the surrounding air of the incontinence device 41 can be arranged. It is also possible to arrange a separate air-exchange duct which connects the two air-exchanges 42, 43, only one outlet to the surroundings of the incontinence device 41 from the air-exchange duct 46 having to be arranged. One of the air-exchanges can then be evacuated via the other air-exchanges.

The air-exchange ducts according to the invention do not of course have to extend along the symmetry line of the article in the longitudinal direction but can extend from the air-exchanges to the periphery of the article in any desired manner. Air-exchange ducts which are curved in their plane can also be arranged.

More than two air-exchanges can be arranged; it may be suitable, for example, to arrange an air-exchanges in the crotch portion of the incontinence device 41, and an air-exchange in each end portion.

Figure 5:
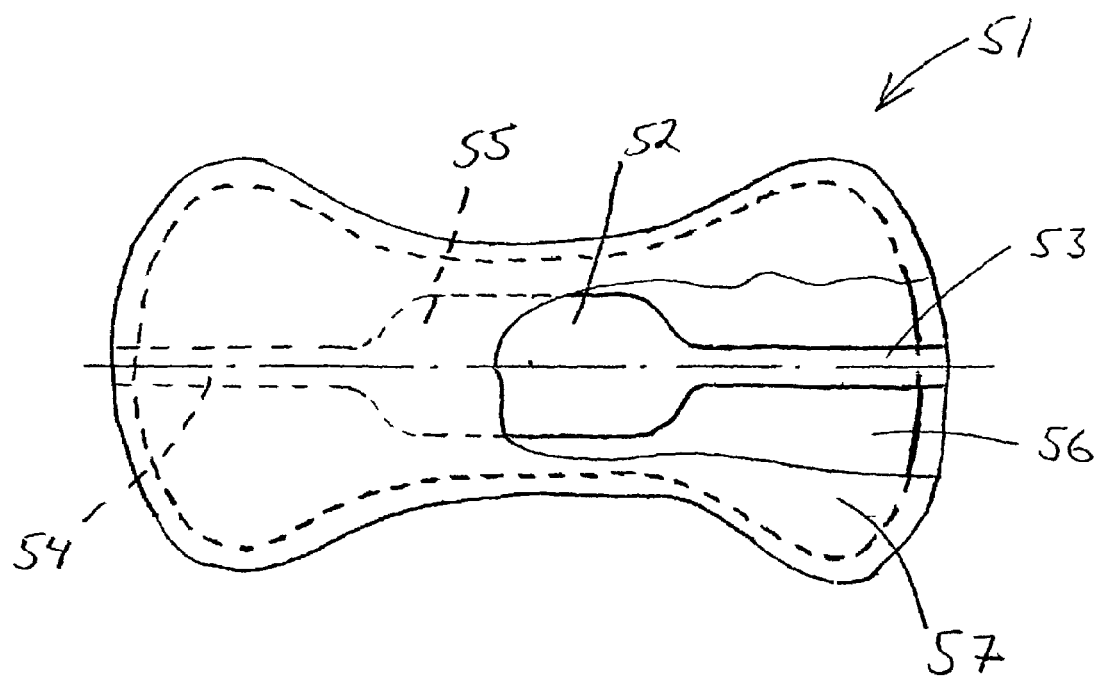
FIG. 5 shows an incontinence device for light incontinence according to a fourth embodiment of the invention, seen from the side which is intended to face away from the wearer during use.

FIG. 5 shows an incontinence device 51 according to a fourth embodiment, from the side which is intended to face away from the wearer during use. In order to show components which are important for the invention more clearly, a part of the liquid-impermeable backsheet 57 has not been illustrated in the figure.

In the incontinence device 51, the air-exchange 52 and the two air-exchange ducts 53, 54 consist of an integrated air-exchange system 55. The air-exchange system 55 consists of a profile-cut material piece comprising an open synthetic wadding made of, for example, polyester fibres or another open and resilient material. The entire air-exchange system 55 is arranged between the absorption body 56 and the liquid-impermeable backsheet 57. One advantage of an integrated air-exchange system 55 according to this embodiment, which extends in the longitudinal direction of the incontinence device 51 along the entire length of the incontinence device 51, is that all the parts which are part of the air-exchange system 55 are comprised in one and the same web-shaped material.

During the manufacture of incontinence devices 51, the web-shaped material which constitutes the air-exchange system 55 is usually stored in the form of a roll material, usually arranged at the side of or behind the manufacturing machine. The material stored on a roll is sufficient for air-exchange systems 55 for a large number of incontinence devices 51. The web-shaped material is initially profile-cut in a separate cutting process and is then applied to the future incontinence device 51. The web-shaped material is finally separated in the transverse direction together with other web-shaped materials included in the incontinence device 51 when individual incontinence devices are cut/separated from one another.

Figure 6:
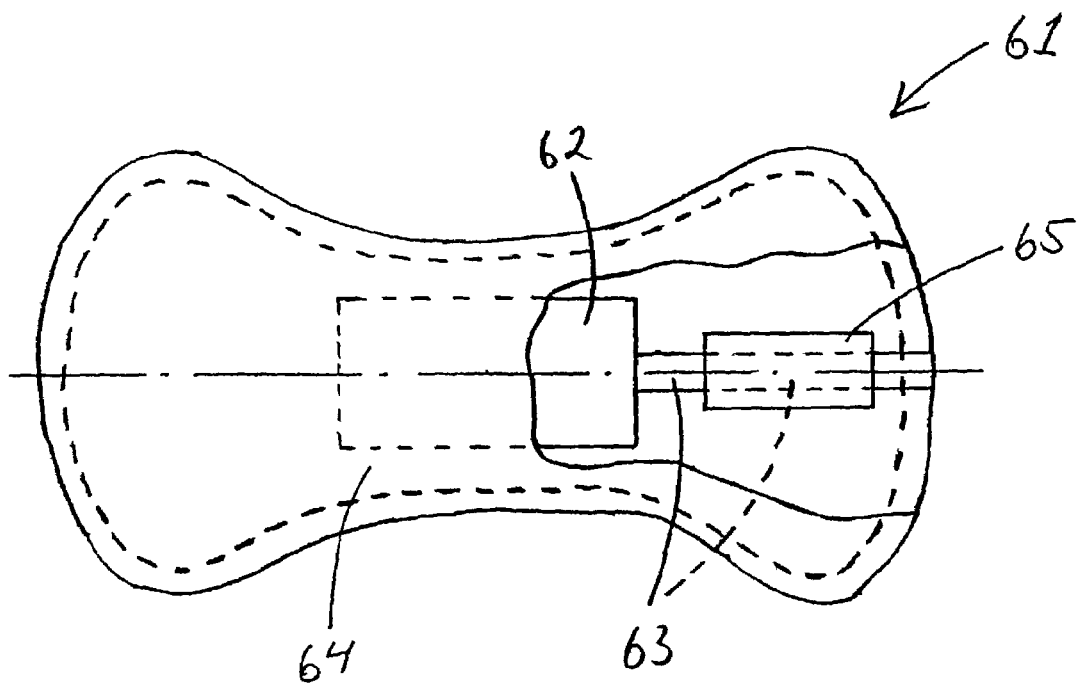
FIG. 6 shows an incontinence device for light incontinence according to a fifth embodiment of the invention, seen from the side which is intended to face away from the wearer during use.

FIG. 6 shows an incontinence device 61 according to a fifth embodiment, from the side which is intended to face away from the wearer during use. In order to show components which are important for the invention more clearly, a part of the liquid-impermeable backsheet 64 has not been illustrated in the figure. The incontinence device 61 is constructed in the same way as the incontinence device 1 according to the first embodiment with regard to design and positioning of the air-exchange 62 and the air-exchange duct 63.

A moisture trap 65 is arranged between the liquid-impermeable backsheet 64 of the incontinence device 61 and the air-exchange duct 63. The function of the moisture trap 65 is to absorb small quantities of liquid which may follow when air is pressed out of the air-exchange 62 through the air-exchange duct 63 so that there is no risk of liquid coming out through the outlet of the air-exchange duct 63 into the surroundings of the incontinence device 61. The moisture trap 65 suitably has an extension in the longitudinal direction of the air-exchange duct 63 of at least 3 centimetres in order that it is likely that any liquid transported in the air-exchange duct 63 will be absorbed.

The moisture trap 65 consists of a fine-capillary hydrophilic material which rapidly absorbs the liquid transported in the air-exchange duct 63. Suitable materials for the moisture trap 65 are compressed fine-capillary cellulose fluff pulp, tissue material or the like.

The incontinence device 61 can be provided with a number of moisture traps 65, suitably arranged at a distance behind one another along the extension of the air-exchange duct 63. One or more moisture traps can also be arranged between the air-exchange 62 and the liquid-impermeable backsheet 64 of the incontinence device 61, and small quantities of liquid can then be absorbed by the moisture trap before the air in the air-exchange 62 is pressed out of the incontinence device 61.

Figure 6B:
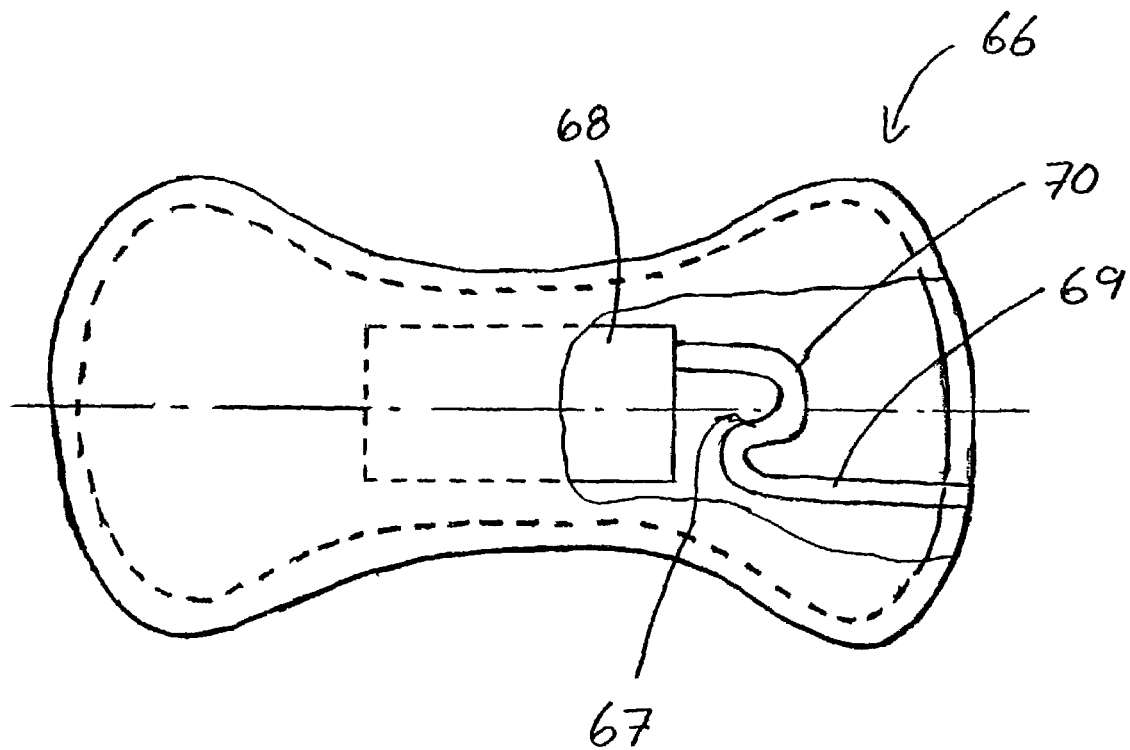
FIG. 6b shows an incontinence device for light incontinence according to a sixth embodiment of the invention, seen from the side which is intended to face away from the wearer during use.

FIG. 6b shows an incontinence device 66 according to a sixth embodiment, from the side which is intended to face away from the wearer during use, comprising an alternative embodiment of a moisture trap 67. In order to show components which are important for the invention more clearly, a part of the liquid-impermeable backsheet has not been illustrated in the figure. The moisture trap 67 is especially suitable when there is a risk of the air-exchange 68 of the incontinence device 66 containing somewhat larger quantities of liquid which, when the air-exchange 68 is compressed rapidly, threaten to flow through the air-exchange duct 69 in the form of a sprinkling or drops. The moisture trap 67 consists of an S-shaped curve 70 of the air-exchange duct 69, the sprinkling or the drops not being capable of passing through the S-shaped curve 70 without encountering the walls of the air-exchange duct 69 in one or more places and then being absorbed by the absorption material which is arranged adjacent to the S-shaped curve 70. The curve can of course be designed with a geometry other than an S-shape.

Figure 7:
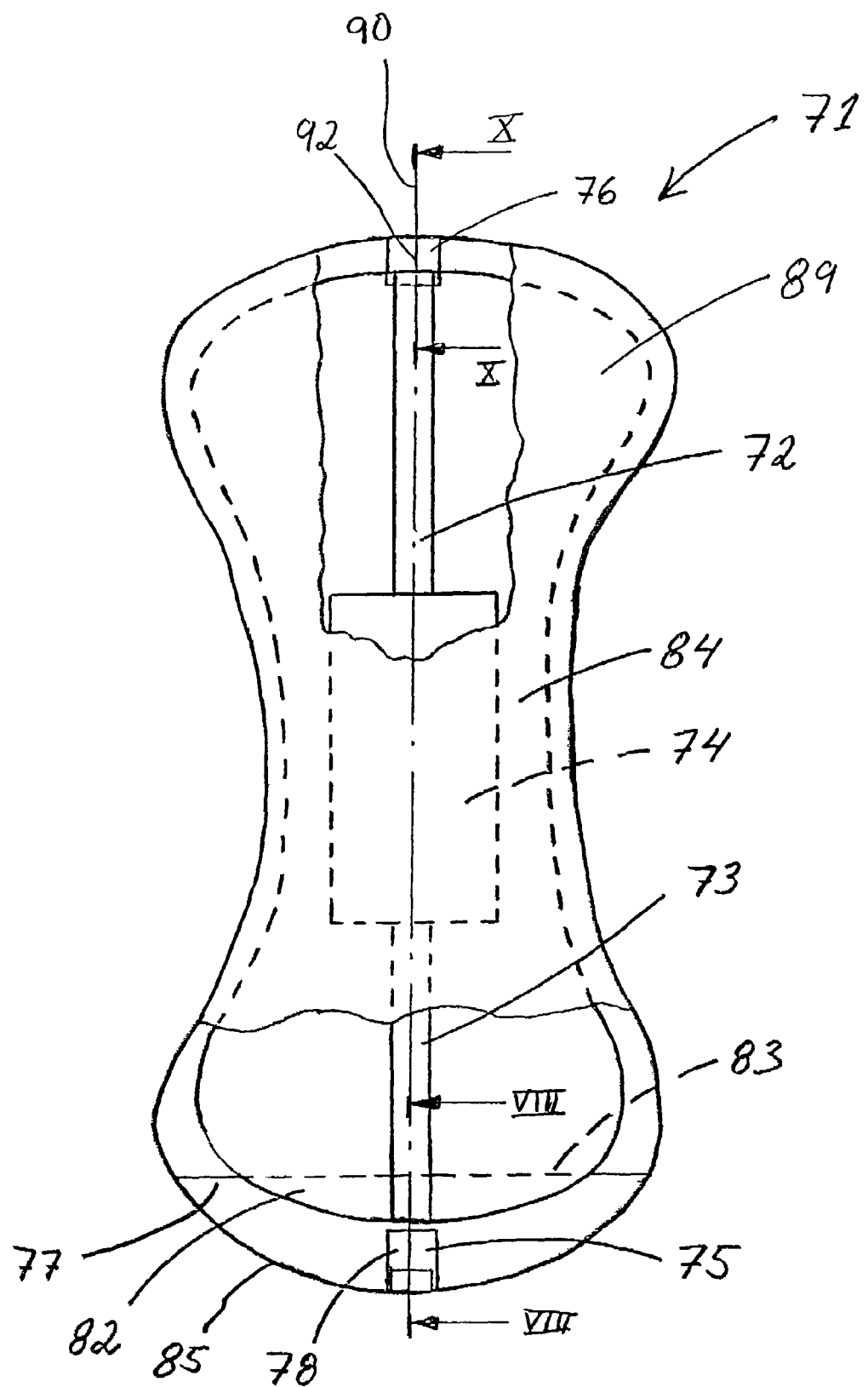
FIG. 7 shows an incontinence device for light incontinence according to a seventh embodiment of the invention, seen from the side which is intended to face away from the wearer during use.

FIG. 7 shows an incontinence device 71 according to a seventh embodiment of the invention, from the side which is intended to face away from the wearer during use. In order to show components which are important for the invention more clearly, a part of the liquid-impermeable backsheet has not been illustrated in the figure. The incontinence device 71 comprises one air-exchange 74 and two air-exchange ducts 72, 73.

Arranged in air communication with one air-exchange duct 73 is an inflow valve 75, the inflow valve 75 stopping the passage of air out of the air-exchange 74 through the air-exchange duct 73 and allowing the passage of air which flows into the air-exchange 74 via the air-exchange duct 73.

Arranged in air communication with the other air-exchange duct 72 is an outflow valve 76, the outflow valve 76 allowing the passage of air which flows out of the air-exchange 74 via the air-exchange duct 72 and stopping the passage of air into the air-exchange 74 via the air-exchange duct 72. The arrangement of an outflow valve 76 in air communication with one air-exchange duct 72 of the incontinence device 71 and an inflow valve 75 in air communication with the other air-exchange duct 73 of the incontinence device 71 means that all air transport takes place in the same direction through the incontinence device 71, that is away from the inflow valve 75, via the air-exchange duct 73, the air-exchange 74 and the air-exchange duct 72, finally to leave the incontinence device 71 via the outflow valve 76.

One advantage of an incontinence device 71 comprising an inflow valve 75 and an outflow valve 76 is that the risk of air which has just left the incontinence device 71 being sucked back into the incontinence device 71 immediately is eliminated. Another advantage is that the volume ratio between the air-exchange 74 and the air-exchange ducts 72, 73 is not critical because the risk of the same air pulsating between the air-exchange 74 and the air-exchange ducts 72, 73 throughout the whole time in use is eliminated owing to the fact that air moves in a predetermined direction through the air-exchange 74 and the air-exchange ducts 72, 72 and is prevented from flowing in the opposite direction.

Figure 8:
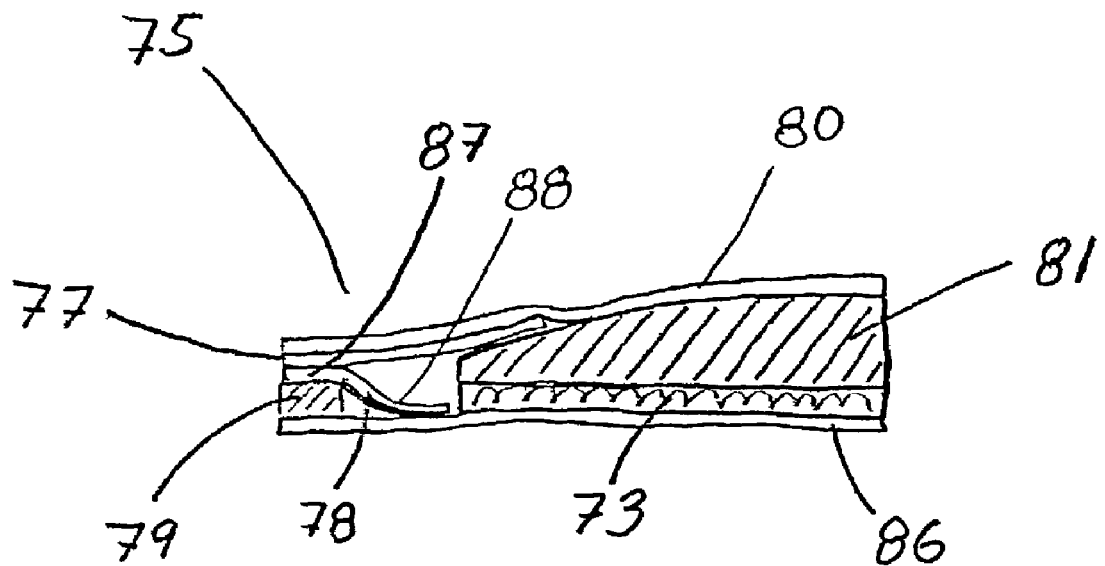
FIG. 8 shows an enlarged cross section of a closed inflow valve according to the embodiment shown in FIG. 7.
Figure 9:
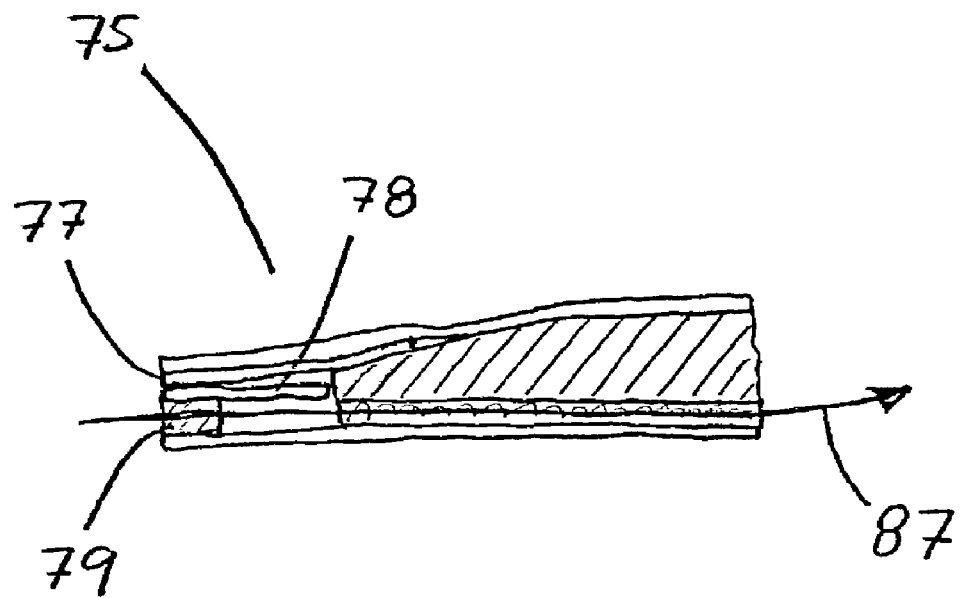
FIG. 9 shows an enlarged cross section of an open inflow valve according to the embodiment shown in FIG. 7.
Figure 10:
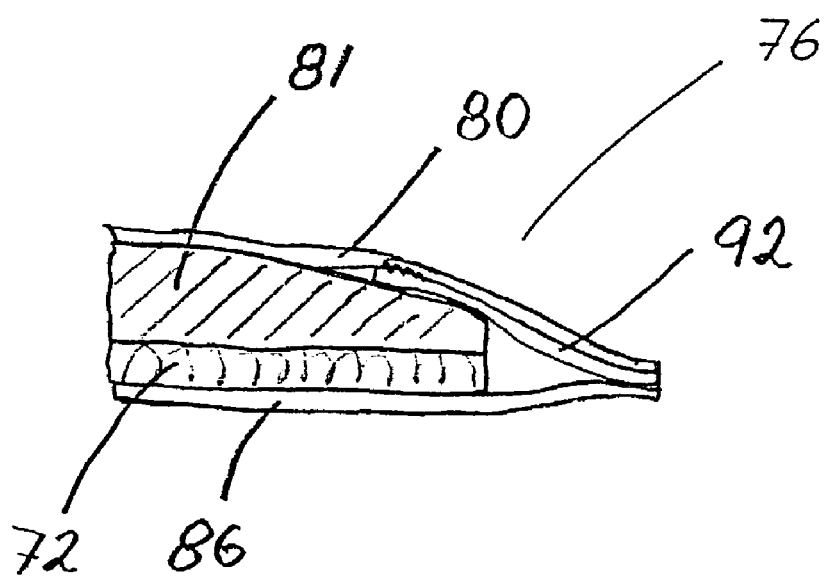
FIG. 10 shows an enlarged cross section of a closed outflow valve according to the embodiment shown in FIG. 7.
Figure 11:
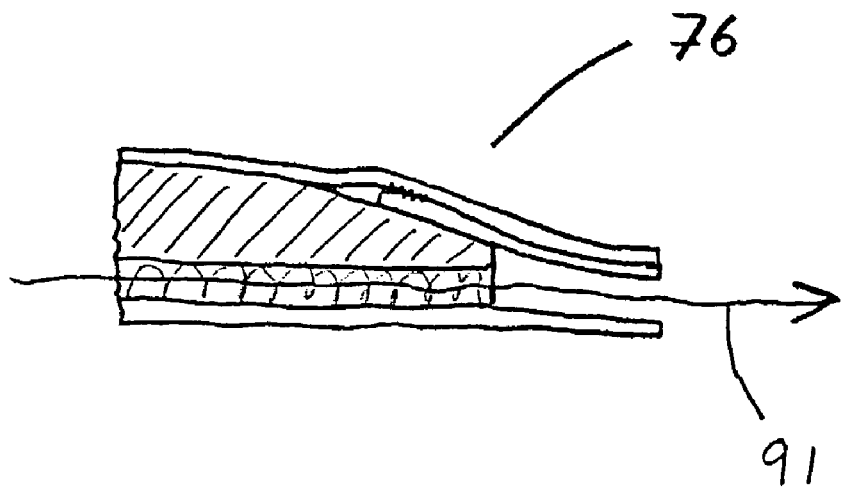
FIG. 11 shows an enlarged cross section of an open outflow valve according to the embodiment shown in FIG. 7.

FIGS. 7, 8, 9, 10 and 11 show the inflow valve 75 and the outflow valve 76. FIGS. 8 and 9 show an enlarged cross-sectional view (VIII-VIII) through the inflow valve 75 arranged for inflowing air, and FIGS. 10 and 11 show an enlarged cross-sectional view (X-X) through the outflow valve 76 arranged for outflowing air. FIG. 8 shows the outflow valve 75 in a closed state, and FIG. 9 shows the same valve 75 in an open state when air flows into the incontinence device 71.

The inflow valve 75 comprises a sealing piece 77, a membrane 78 and a distance element 79. The inflow valve 75 is arranged in one end portion 82 of the incontinence device 71, essentially between the extensions of the liquid-permeable cover layer 80 and of the liquid-impermeable backsheet 86 in the longitudinal direction outside the absorption body 81, the layers 80, 86 being connected via the inflow valve 75 in the area where the inflow valve 75 is arranged, and the liquid-permeable cover layer 80 and the liquid-impermeable cover layer 86 being interconnected directly within other parts of those portions of the two layers 80, 86 located outside the absorption body 81.

The sealing piece 77 is arranged on that surface of the liquid-permeable cover layer 80 of the incontinence device 71 which is oriented towards the absorption body 81 and has a straight edge 83 (FIG. 7) oriented towards the crotch portion 84 of the incontinence device 71 and a curved edge 85 having the same curved shape as the end portion 82 of the incontinence device 71. The sealing piece 77 is connected to the liquid-permeable cover layer 80 by glue or the like over its entire surface. The sealing piece 77 prevents air from flowing out of the air-exchange duct 73 in the wrong direction, that is through the liquid-permeable cover layer 80, when the air-exchange 74 of the incontinence device 71 is compressed. The sealing piece 77 can consist of a number of different materials. It is most usual for the sealing piece 77 to consist of a thin impermeable plastic film, but it is also possible to use other types of impermeable material. The liquid-permeable cover layer 80 can also be sealed in the end portion 82 of the incontinence device 71 by virtue of the cover layer 80 being coated with, for example, impermeable glue. Sealing the opposite surface of the cover layer 80, that is the surface which is intended to face the wearer during use, is also possible in the end portion 82 of the incontinence device 71.

The distance element 79 is arranged between the sealing piece 77 and the backsheet 86, the distance element 79 ensuring that the incontinence device 71 maintains a free passage for inflowing air. The distance element 79 suitably comprises an open synthetic wadding made of, for example, polyester fibres, air being capable of passing easily though the distance element. Materials other than polyester fibres are of course possible as the main component of the distance element 79. Examples of other fibre qualities are polypropylene fibres and polyethylene fibres. Mixtures of different synthetic fibre sorts are also possible.

It is also possible to select materials other than open hydrophobic synthetic wadding materials as the main component of the distance element 79. An example of a suitable material is foamed plastic with cells which are open and in air communication with one another and with the surroundings.

The inflow valve 75 also comprises a membrane 78, the membrane 78 closing when air tries to pass out of the incontinence device 71 and opening when air tries to flow into the incontinence device 71. The membrane 78 consists of an impermeable, thin and flexible plastic film. The membrane 78, which is rectangular in shape, is fastened at one 87 of its short ends arranged at one transverse edge 85 of the incontinence device 71, and is free at its other end 88 arranged towards the crotch portion 84 of the incontinence device 71, the free end 88 of the membrane closing for air which tries to pass out of the incontinence device 71 and opening for air which tries to pass into the incontinence device 71. FIG. 8 shows how the membrane 78 is arranged when the inflow valve 75 is closed, and FIG. 9 shows the position of the membrane when the inflow valve 75 is open. Inflowing air is shown by the arrow 87 in FIG. 9.

FIG. 10 shows the outflow valve 76 in a closed state, and FIG. 11 shows the same valve 76 in an open state when air flows out of the incontinence device 71.

The outflow valve 76 comprises a membrane 92 arranged in the end portion 89 of the incontinence device 71. The membrane 92 is essentially rectangular and arranged mainly between the extensions of the liquid-permeable cover layer 80 and of the liquid-impermeable backsheet 86 in the longitudinal direction outside the absorption body 81. The membrane 92 is arranged on that surface of the liquid-permeable cover layer 80 of the incontinence device 71 which is oriented towards the absorption body 81. The membrane 92 is connected to the liquid-permeable cover layer 80 by glue or the like over its entire surface. The membrane 92 can consist of a number of different materials. It is most suitable for the membrane 92 to consist of a thin impermeable plastic film, but it is also possible to use other types of impermeable material. The membrane 92 is not connected to the backsheet 86, at least not in an area close to the longitudinal centre line 90 of the membrane 92. When air is pressed towards the outflow valve 76 from the air-exchange duct 72, a gap is formed between the membrane 92 and the backsheet 86 where the membrane 92 and the backsheet 86 are not interconnected, the air being able to pass through the outflow valve 76. FIG. 11 shows the outflow valve 76 when air flows through the outflow valve 76. The air flow is marked by the arrow 91.

The outflow valve 76 is not absolutely necessary in order to bring about acceptable air exchange in the incontinence device 71. An absorbent article 71 provided with only an inflow valve 75 functions satisfactorily with regard to the flow of air in one direction through the incontinence device 71. However, small volumes of air tend to flow into the air-exchange duct 72, intended for outflowing air, via the liquid-permeable cover layer 80 of the incontinence device 71. For an incontinence device without an outflow valve, it is important that the incontinence device 71 has a short break in the connection between the liquid-permeable cover layer 80 and the liquid-impermeable backsheet 86 adjacent to the outlet of the air-exchange duct 72 arranged for outflowing air.

The invention also includes all conceivable combinations of the illustrative embodiments described.

Furthermore, the invention is not limited to the illustrative embodiments above, but can of course be applied to other embodiments within the scope of the patent claims below.

The invention claimed is:

1. An absorbent article comprising:
   an upper, liquid-permeable cover layer,
   a lower, liquid-impermeable backsheet,
   an absorbent body arranged between the cover layer and the backsheet, and
   an air-exchange system arranged between the cover layer and the backsheet comprising at least one air-exchange and at least one air-exchange duct having a longitudinal extension and a cross-sectional area,
   wherein said at least one air-exchange duct provides two-way air communication between the air-exchange and the surroundings of the absorbent article such that said at least one air-exchange duct defines an air inlet wherein air from the surroundings enters the air-exchange and said at least one air-exchange duct defines an air outlet wherein air exits the air-exchange through said at least one air-exchange duct,
   wherein the air-exchange is compressible and resilient in all directions, essentially non-absorbent and air-permeable, said air-exchange being in direct contact with the absorption body over a contact surface such that the contact surface is open with regard to air communication between the air exchange and the absorption body; and
   wherein the air-exchange duct comprises a compressible and resilient, essentially non-absorbent material, and displays air-permeability.

2. The absorbent article according to claim 1, wherein the volume of the air-exchange is at least two times greater than the volume of the air-exchange duct.

3. The absorbent article according to claim 2, wherein the volume of the air-exchange is at least five times greater than the volume of the air-exchange duct.

4. The absorbent article according to claim 2, wherein the volume of the air-exchange is at least seven times greater than the volume of the air-exchange duct.

5. The absorbent article according to claim 1, wherein the air-exchange comprises an essentially non-absorbent hydrophobic fibre wadding.

6. The absorbent article according to claim 5, wherein the capillaries of the air-exchange are larger than the capillaries of the absorbent body.

7. The absorbent article according to claim 1, wherein the air-exchange comprises an essentially non-absorbent foamed plastic having open cells.

8. Absorbent article according to claim 1, wherein the entire contact surface between the air-exchange and the absorbent body is open with regard to air communication.

9. The absorbent article according to claim 1, wherein the air-permeable non-absorbent material of the air-exchange duct comprises an essentially non-absorbent hydrophobic fibre wadding.

10. The absorbent article according to claim 1, wherein the air-permeable non-absorbent material of the air-exchange duct comprises an essentially non-absorbent foamed plastic comprising open cells.

11. The absorbent article according to claim 1, wherein the air-permeable non-absorbent material of the air-exchange duct consists of a flexible thin tube.

12. The absorbent article according to claim 1, wherein the absorbent article has two air-exchange ducts extending from the air-exchange to two different places on the periphery of the absorbent article.

13. The absorbent article according to claim 1, wherein at least one absorbent material piece is arranged between the air-exchange duct and the liquid-impermeable backsheet.

14. The absorbent article according to claim 1, wherein the air-exchange duct has a curved extension.

15. The absorbent article according to claim 14, wherein the curve has an S-shape.

16. The absorbent article according to claim 1, wherein the absorbent article is a baby diaper, the air-exchange having a length within the range 5-25 cm, a width within the range 3-12 cm and a thickness within the range 0.3-3 cm.

17. The absorbent article according to claim 1, wherein the absorbent article is an incontinence device, the air-exchange having a length within the range 10-50 cm, a width within the range 3-15 cm and a thickness within the range 0.3-3 cm.

18. The absorbent article according to claim 1, wherein the absorbent article is a sanitary towel or an incontinence device for use for light incontinence, the air-exchange having a length within the range 2-20 cm, a width within the range 2-8 cm and a thickness within the range 0.2-3 cm.

19. The absorbent article according to claim 1, wherein, upon compression of the air exchange, air is discharged out from the absorbent article by way of said at least one air-exchange duct and wherein, upon expansion of the air exchange, air surrounding the absorbent article is drawn therein by way of said at least one air-exchange duct, thereby defining two-way air communication between the air-exchange and the surroundings of the absorbent article through said at least one air-exchange duct.

20. The absorbent article according to claim 1, wherein air from the surroundings both enters the air-exchange and exits the air-exchange directly through the same said at least one air-exchange duct.

* * * * *